United States Patent

Nadaud et al.

Patent Number: 6,093,409
Date of Patent: *Jul. 25, 2000

[54] MELATONIN DERIVATIVES AND ANTI-FREE-RADICAL DERMOCOSMETICS COMPRISED THEREOF

[75] Inventors: Jean-François Nadaud, Clamart; Christian Colin, Paris, both of France

[73] Assignee: Societe L'Oreal S.A., Paris, France

[ * ] Notice: This patent issued on a continued prosecution application filed under 37 CFR 1.53(d), and is subject to the twenty year patent term provisions of 35 U.S.C. 154(a)(2).

This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/900,832

[22] Filed: Jul. 25, 1997

[30] Foreign Application Priority Data

Jul. 25, 1996 [FR] France ..... 96 09389

[51] Int. Cl.⁷ ............. A61K 6/00; C07D 209/16
[52] U.S. Cl. ............ 424/401; 424/59; 424/70.1; 424/70.5; 514/415; 548/504
[58] Field of Search ............ 514/415; 548/504; 424/401, 70.1, 70.5, 59

[56] References Cited

U.S. PATENT DOCUMENTS

| 4,746,674 | 5/1988 | Pierpaoli et al. | 514/415 |
| 5,560,917 | 10/1996 | Cohen et al. | 424/401 |

FOREIGN PATENT DOCUMENTS

86/05093  9/1986  WIPO .
97/06779  2/1997  WIPO .

OTHER PUBLICATIONS

Brazilian J. Med. Biol. Res., vol. 26, No. 11, 1993, pp. 1141–1155.
Ann. N.Y. Acad. Sci., vol. 786, 1996, pp. 362–378.
Neurosci. Biobehav. Rev., vol. 17, No. 3, 1993, pp. 347–357.
Adv. Exp. Med. Biol., vol. 3398, 1996, pp. 307–313.
Advances in Pineal Research, vol. 7, 1994, pp. 211–228.

*Primary Examiner*—Thurman K. Page
*Assistant Examiner*—Lakshmi Channavajjala
*Attorney, Agent, or Firm*—Burns, Doane, Swecker & Mathis, L.L.P.

[57] ABSTRACT

Topically applicable dermocosmetic compositions for combating the clinical signs of skin aging and/or for improving the appearance of the skin, the scalp or the hair, comprise an anti-free-radical effective amount of at least one novel melatonin derivative having the structural formula (I):

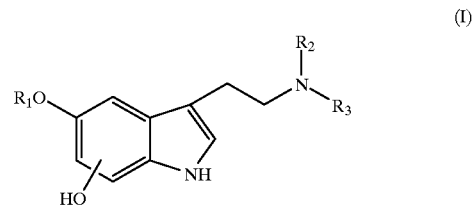

in which $R_1$ is a lower alkyl radical, $R_2$ is a hydrogen atom or a lower alkyl radical, and $R_3$ is a hydrogen atom or a lower acyl radical, with the proviso that the hydroxyl radical is in the 4-, 6- or 7-position on the indole ring system, or a physiologically acceptable salt, solvate or bioprecursor/prodrug thereof, formulated into a topically applicable, cosmetically/dermatologically acceptable vehicle, carrier or diluent therefor.

1 Claim, No Drawings

MELATONIN DERIVATIVES AND ANTI-FREE-RADICAL DERMOCOSMETICS COMPRISED THEREOF

CROSS-REFERENCE TO COMPANION APPLICATIONS

Copending applications Ser. No. 08/900,828, U.S. Pat. No. 5,932,608 and Ser. No. 08/900,109, each filed concurrently herewith and each assigned to the assignee hereof.

BACKGROUND OF THE INVENTION

1. Technical Field of the Invention

The present invention relates to novel melatonin derivatives having improved anti-free-radical (AFR) activity, and to topically applicable dermocosmetic compositions comprised thereof; the subject compositions are well suited for combating the clinical signs of human skin aging and/or for improving the appearance of the skin, the scalp or the hair.

2. Description of the Prior Art

Over the course of time, different signs and conditions appear on the skin and/or on the scalp and/or on the hair, which are very characteristic of aging, reflected, in particular, by a modification of the skin structure and functions.

The principal clinical signs of aging of the skin are, especially, the appearance of fine lines and deep wrinkles which increase or are accentuated with age. Moreover, the skin complexion is generally modified and diffuse irritations and occasionally telangiectasias may exist on certain areas of the skin. Another clinical sign of aging is the dry and coarse appearance of the skin, which is due essentially to more considerable desquamation. Lastly, a loss of firmness and tonicity of the skin are observed, which, as for the wrinkles and fine lines, is at least partly explained by dermal and epidermal atrophy, as well as by a flattening of the formation. It is thus observed that the clinical signs of aging of the skin result essentially from dysfunction of the principal biological mechanisms involved in the skin.

Free radicals are known factors responsible for the aging of cells, in particular the skin. They originate principally from molecular oxygen and are induced, for example, by atmospheric pollutants and/or by ultraviolet radiation.

The following free radicals are particularly representative:

(a) singlet oxygen, which is very oxidative, very toxic and has a very short lifetime, produced by the excitation of molecular oxygen by light photons;

(b) the superoxide anion radical, produced by the addition of an electron to oxygen and which enables the production of very reactive hydroxyl radicals;

(c) the hydroxyl radical, which is very oxidative and the most toxic to cells.

Also illustrative are lipoperoxide radicals which are the oxidation products of membrane lipids and extracellular iron, which, by reacting with hydrogen peroxide and the superoxide anion radical accumulated outside the cell, will promote the production of hydroxyl radicals.

Preventing or treating the damage caused on the skin, scalp or the hair by free radicals, in particular aging of the skin, whether intrinsic or extrinsic aging, and the clinical signs indicated above, is essentially a matter of maintaining or improving the appearance of the skin, the scalp or the hair.

Various active agents have been described as possessing AFR properties, as well as their use in cosmetics. These are compounds such as tocopherols, for example vitamin E, which are known to possess both antioxidant properties with respect to the phospholipids of the cell membrane and anti-free-radical (AFR) properties (J. B. Chazan and M. Szulc, *Cah. Nutr. Diet.*, 6 XXII—1, 66–76 (1987)) or superoxide dismutases, for example those extracted from bovine erythrocytes (Markovitz, *J. Biol. Chem.*, 40, 234 (1959)), from *Escherichia coli* (Keele and Fridovich, *J. Biol. Chem.*, 245, 6176 (1970)) or from marine bacterial strains (FR 73/13670), or, alternatively, melatonin.

Melatonin, or N-acetyl-5-methoxytryptamine, which is particularly well known for its circadian activity in regulating the production of hormones, is also indicated for its antioxidant activity (Reiter R. J., *Verhandung der Deutschen Zoologischen Gesellschaft*, 87 (2), 195–204 (1994); Reiter R. J. et al., *Neuroendocrinoll Letter*, 15 (1–3), 103–113 (1993); Reiter R. J. et al., *J. Pineal Res.*, 18 (1), 1–11 (1995)), in particular its AFR activity (Reiter R. J. et al., *Brazilian Journal of Medical and Biological Research*, 26 (22), 1141–1155 (1993)). Melatonin has also been described for its dermocosmetic properties in order to improve the appearance of the skin (JP-61/221,104; U.S. Pat. No. 4,746,674), or to protect the skin against the effects of irradiation with UV rays (EP-0,438,856; E. Bangha et al., *Dermatology* 191, [2], 176 (1995)). Most of the studies on melatonin relate to the oxidation phenomena associated with aging of the brain (Poeggeler B. et al., *J. Pineal Res.*, 14(4), 151–168 (193); Cagnoli C. M. et al., *J. Pineal Res.*, 18 (4), 222–226 (1995); Melchiorri D. et al., *Faseb J.*, 9 (12), 1205–1210 (1995); Sewerynek E. et al., *Neuroscience Letters*, 195 (3), 203–205 (1995)) and it appears that melatonin is more effective than common AFR active agents such as vitamin E (Pieri C. et al., *Life Sciences*, 55 (15), 271–276 (1994)).

SUMMARY OF THE INVENTION

It has now unexpectedly been determined that certain melatonin derivatives exhibit enhanced anti-free-radical activity vis-a-vis melatonin.

Briefly, the present invention features novel melatonin derivatives having the structural formula (I):

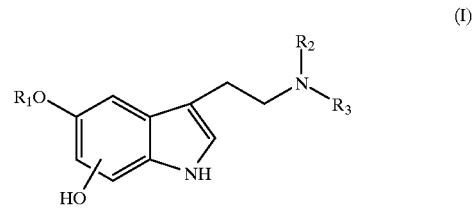

(I)

in which $R_1$ is a lower alkyl radical; $R_2$ is a hydrogen atom or a lower alkyl radical; and $R_3$ is a hydrogen atom or a lower acyl radical, with the hydroxyl radical on the indole ring system being in the 4-, 6-or 7-position, as well as the physiologically acceptable salts, solvates or bioprecursors (prodrugs) thereof.

DETAILED DESCRIPTION OF BEST MODE AND SPECIFIC/PREFERRED EMBODIMENTS OF THE INVENTION

More particularly according to the present invention, the subject novel compounds advantageously have the structural formula (Ia):

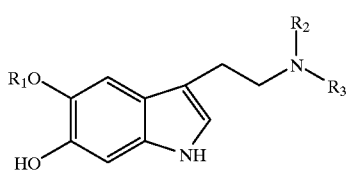

(Ia)

in which $R_1$, $R_2$ and $R_3$ are as defined above and the hydroxyl radical is in position 6.

By the term "lower alkyll" is preferably intended linear or branched $C_1$ to $C_4$ alkyl radicals optionally substituted with one or more halogen atoms (F, Cl or Br). These are, in particular, methyl, ethyl, propyl or butyl radicals. This definition also applies to the alkyl moieties of the acyl radicals.

By the term "salt" is intended any addition salt of a physiologically acceptable inorganic or organic acid, which is common for cosmetically or dermatologically active compounds, such as addition salts with hydrochloric acid, sulfuric acid, acetic acid, citric acid, fumaric acid, hemisuccinic acid, maleic acid, and the like.

By the term "physiologically acceptable bioprecursor" is intended any derivative or prodrug capable of liberating the compounds of general formula (I) once they have been administered, in particular the esters, such as alkyl phosphates, alkyl sulfates or acyls (for example acetate) or the monosaccharides (in particular glucosyl, mannosyl, fructosyl, N-acetylglucamine or galactosyl) of the hydroxyl radical.

Preferably, $R_1$ is a methyl radical, $R_2$ is a hydrogen atom and $R_3$ is an acetyl radical.

The melatonin derivatives of formula (I) are facilely prepared by adapting known syntheses, for example the general techniques described in J. Szmuszkovicz, "Synthesis of N-acetyl-5-methoxy-tryptamine," *J. Org. Chem.*, 25, 857 (1960), J. Supniewski et al., "Synthesis of melatonin (5-methoxy-N-acetyltryptamine," published in *Bull. Acad. Polon. Sci. Ser. Biol.*, 8, pp. 479–481 (1960); or Mashkovsky et al. in *Farmakol. Toksikol.*, 26, n 1, 10 (1963). Cf. WO-86/05093.

The present invention also features the formulation of the melatonin derivatives of general formula (I), as anti-free-radical active agents, into cosmetic compositions for improving the appearance of the skin, the scalp or the hair.

The subject compositions are preferably cosmetic compositions for controlling the damage caused by free radicals on the skin, the scalp or the hair. Thus, the present invention also features a cosmetic treatment or regimen which entails improving the appearance of the skin, the scalp or the hair, by applying topically to the skin and/or the scalp and/or the hair a composition comprising, as an anti-free-radical active agent, an effective amount of a melatonin derivative as described above.

However, the subject compositions may also be dermatological compositions and, in this event, the present invention also features the formulation of melatonin derivatives as described above into pharmaceutical compositions for the dermatological treatment of the clinical signs of aging of the skin associated with damage caused by free radicals.

Lastly, the present invention features cosmetic compositions for improving the appearance of the skin, the scalp or the hair, comprising at least one melatonin derivative as described above, as an anti-free-radical active agent, formulated into a cosmetically acceptable vehicle, diluent or carrier therefor.

In these compositions, the melatonin derivative according to the invention is advantageously present in an amount of less than 10% by weight relative to the total weight of the composition. In general, the amount of melatonin derivatives ranges from 0.0001% to 10% by weight, in particular an amount ranging from 0.0005% to 1% by weight, more particularly an amount less than 0.1%, for example about 0.01%.

It should be appreciated, however, that the melatonin derivatives are active in amounts of less than $10^{-4}\%$ by weight, down to as little as $10^{-14}\%$ by weight.

The cosmetic or dermatological compositions into which the subject melatonin derivatives are formulated may exist in any pharmaceutical form for topical application which is normal in this art. The subject compositions may be in the form, in particular, of an aqueous solution or an oily suspension or a dispersion of the lotion or serum type, emulsions of liquid or semi-liquid consistency of the milk type, obtained by dispersing a fatty phase in an aqueous phase (O/W) or, conversely, (W/O), or suspensions or emulsions of soft consistency of the aqueous or anhydrous cream or gel type, or, alternatively, microcapsules or microparticles, or vesicle dispersions of ionic and/or non-ionic type. These compositions are formulated via the usual techniques.

The amounts of the various constituents of the subject compositions are those conventionally employed in the art.

Such compositions, in particular, constitute cleansing, protecting, treatment or care creams for the face, for the hands, for the feet, for the major anatomical folds or for the body (for example day creams, night creams, makeup-removing creams, foundation creams and antisun/sunscreen creams), fluid foundations, makeup-removing milks, protective or care body milks, sunscreen milks, skin care lotions, ointments, gels or mousses such as cleansing lotions, sunscreen lotions or artificial tanning lotions, compositions for the bath, deodorizing compositions comprising a bactericidal agent, aftershave gels or lotions, hair-removing creams, etc.

The compositions according to the invention may also comprise solid preparations constituting cleansing soaps or bars.

The subject compositions may also be packaged in the form of an aerosol composition also comprising a propellant under pressure.

When the composition is an emulsion, the proportion of the fatty phase may range from 5% to 80% by weight, and preferably from 5% to 50% by weight, relative to the total weight of the composition. The oils, waxes, emulsifiers and co-emulsifiers formulated into the compositions in emulsion form are selected from among those conventionally employed in the cosmetics art. The emulsifier and the co-emulsifier are advantageously present in the composition in a proportion ranging from 0.3% to 30% by weight, and preferably from 0.5% to 20% by weight, relative to the total weight of the composition. The emulsion may also contain lipid vesicles.

When the composition is an oily gel or solution, the fatty phase may represent more than 90% of the total weight of the composition.

In known manner, the cosmetic or dermatological composition may also contain additives and adjuvants that are common in the cosmetic or dermatological arts, such as hydrophilic or lipophilic gelling agents, hydrophilic or lipophilic additives, preservatives, antioxidants, solvents, fragrances, fillers, screening agents, odor-absorbers and dyestuffs and colorants. The amounts of these various additives and adjuvants are those conventionally used in these fields and, for example, constitute from 0.01% to 10% of the total weight of the composition. Depending on their nature, these additives and adjuvants may be introduced into the fatty phase, into the aqueous phase and/or into the lipid spherules.

Exemplary oils or waxes which may be incorporated in the compositions of the invention include mineral oils (liquid petroleum jelly), plant oils (liquid fraction of karite butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils.

Exemplary emulsifiers include, for example, glyceryl stearate, polysorbate 60 and the mixture of PEG-6/PEG-32/glycol stearate marketed under the trademark Tefoseo®63 by Gattefosse.

Exemplary solvents according to the invention include the lower alcohols, in particular ethanol and isopropanol, and propylene glycol.

And exemplary hydrophilic gelling agents according to the invention include carboxyvinyl polymers (carbomer), acrylic copolymers such as acrylate/alkyl acrylate copolymers, polyacrylamides, polysaccharides such as hydroxypropyl cellulose, natural gums and clays, and representative lipophilic gelling agents include the modified clays such as bentones, metal salts of fatty acids such as aluminum stearates, hydrophobic silica, ethyl cellulose and polyethylene.

Insofar as they do not interfere with the activity of the subject melatonin derivatives, the compositions according to the invention may contain other active agents intended, in particular, for the prevention and/or treatment of skin conditions/afflictions.

In order to further illustrate the present invention and the advantages thereof, the following specific examples are given, it being understood that same are intended only as illustrative and in nowise limitative.

EXAMPLE 1

In Vitro Activity

The activity of the melatonin derivatives according to the invention was studied in various AFR tests, for 0.03% solutions, and compared with that of melatonin and those of reference anti-free-radical agents.

For the "Hp-squalene" anti(singlet oxygen $^1O_2$) test (C. Vever-Bizet et al., *Photochemistry and Photobioloqy*, Vol. 50, No. 3, 321–325 (1989); L. P. Srivastava et al., *Photobiochemistry and Photobiophysics*, 11, 129–137 (1986)), 6-hydroxymelatonin had a percentage of inhibition of close to 78%, which was higher than that obtained for melatonin and the other reference singlet-oxygen inhibitors.

The results of this anti-$^1O_2$ test are reported in the Table below:

TABLE

| (Hp-squalene test): | |
|---|---|
| COMPOUND | % INHIBITION |
| 6-Hydroxymelatonin | 78% |
| Quercetin | 72% |
| Cantaxanthin | 67% |
| β-Carotene | 62% |
| Rutin | 51% |
| Melatonin | 45% |
| Astaxanthin | 34% |

Composition Examples

The following examples illustrate specific compositions according to the invention. In said compositions, the proportions indicated are percentages by weight.

EXAMPLE 2

Facial Care Cream (Oil-in-water Emulsion)

| | |
|---|---|
| 6-Hydroxymelatonin | 0.01 |
| Glyceryl stearate | 2.00 |
| Polysorbate 60 (Tween 60 marketed by ICI) | 1.00 |
| Stearic acid | 1.40 |
| Triethanolamine | 0.70 |
| Carbomer | 0.40 |
| Liquid fraction of karite butter | 12.00 |
| Perhydrosqualene | 12.00 |
| Antioxidant | 0.05 |
| Fragrance | 0.5 |
| Preservative | 0.30 |
| Water | qs 100% |

EXAMPLE 3

Facial Care Gel

| | |
|---|---|
| 6-Hydroxymelatonin | 0.001 |
| Hydroxypropylcellulose (Klucel H marketed by Hercules) | 1.00 |
| Antioxidant | 0.05 |
| Isopropanol | 40.00 |
| Preservative | 0.30 |
| Water | qs 100% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating the clinical signs of skin aging in a subject in need of such treatment, comprising topically applying thereto an anti-free radical effective amount of the dermocosmetic composition wherein said dermocosmetic composition comprises an anti-free-radical effective amount of at least one melatonin derivative having structural formula (I):

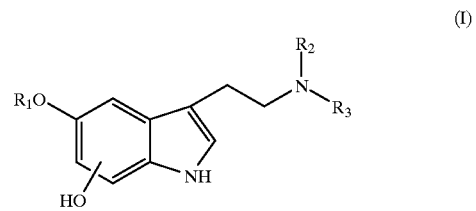

(I)

in which $R_1$ is a lower alkyl radical, $R_2$ is a hydrogen atom or a lower alkyl radical, and $R_3$ is a hydrogen atom or a lower acyl radical, or a physiologically acceptable salt, solvate or bioprecursor/prodrug thereof, with the proviso that the hydroxyl radical is in the 6- or 7-position on the indole ring system, formulated into a topically applicable, cosmetically/dermatologically acceptable vehicle, carrier or diluent therefor, and wherein the amount of said at least one melatonin derivative ranges from $10^{-14}$% to less than $10^{-4}$% by weight.

* * * * *